United States Patent [19]

Nussenzweig et al.

[11] Patent Number: 4,466,917
[45] Date of Patent: Aug. 21, 1984

[54] MALARIA VACCINE

[75] Inventors: Ruth S. Nussenzweig; G. Nigel Godson; Victor Nussenzweig, all of New York, N.Y.

[73] Assignee: New York University, New York, N.Y.

[21] Appl. No.: 234,096

[22] Filed: Feb. 12, 1981

[51] Int. Cl.³ .................. C07G 7/00; C12P 21/00; C12N 15/00
[52] U.S. Cl. .................. 260/112 R; 435/68; 435/172.2; 435/172.3; 424/88; 935/108; 935/65; 935/45; 935/6; 935/22
[58] Field of Search ............ 435/172, 68; 260/112 R; 424/88

[56] References Cited

PUBLICATIONS

Helling et al., Genetic Engineering, by Chakrabanty, CRC Press Inc., pp. 1–30, (1978).
Cohen, Nature, vol. 288, p. 8, Nov. 6, 1980.
Yoshida et al., Science, vol. 207, pp. 71–73, Jan. 4, 1980.
Nandin et al., Nature, vol. 274, pp. 55–57, Jul. 6, 1978.
Todorovic et al., The American Journal of Tropical Medicine and Hygiene, vol. 17, No. 5, pp. 685–694, (1968).
Musoki et al., The Journal of Parasitology, vol. 63, No. 6, pp. 1081–1088, Dec. 1977.
Jepsen et al., Acts Path. Microbiol. Scand., Sect. C, vol. 88, pp. 263–270, (1980).
"Structural Similarities among the Protective Antigens of Sporozoites from Different Species of Malaria Parasites," by Ferricio Santoro, Alan H. Cochrane, Victor Nussenzweig, Elizabeth H. Nardin, Ruth S. Nussenzweig, Robert W. Gwadz, and Arturo Ferreira, *The Journal of Biological Chemistry*, vol. 258, pp. 3341–3345, Mar. 10, 1983.
"Circumsporozoite Proteins of Human Malaria Parasites Plasmodium Falciparum and Plasmodium Vivax," by Elizabeth H. Nardin, Victor Nussenzweig, Ruth S. Nussenzweig, William E. Collins, K. Tranakchit Harinasuta, Pramuan Tapchaisri, and Yaovamarn Chomcharn, *J. Exp. Med.*, vol. 156, pp. 20–30, Jul. 1982.
"Cloning and Expression in *E. coli* of the Malarial Sporozoite Surface Antigen Gene from Plasmodium Knowlesi," by Joan Ellis, Luiz S. Ozaki, Robert W. Gwadz, Alan H. Cochrane, Victor Nussenzweig, Ruth S. Nussenzweig and G. Nigel Godson, *Nature*, vol. 302, pp. 536–538, (Apr. 7, 1983).
"Identification and Chemical Synthesis of a Tandemly Repeated Immunogenic Region of *Plasmodium knowlesi* Circumsporozoite Protein," by G. N. Godson, J. Ellis, P. Svec, D. H. Schlesinger & V. Nussenzweig, *Nature*, vol. 305, pp. 29–33, (Sep. 1, 1983).
"Monoclonal Antibodies Identify the Protective Antigens of Sporozoites of *Plasmodium knowlesi*," by Alan H. Cochrane, Ferrucio Santoro, Victor Nussenzweig, Robert W. Gwadz, and Ruth S. Nussenzweig, *Proc. Natl. Acad. Sci. U.S.A.*, vol. 79, pp. 5651–5655, Sep. 1982.

*Primary Examiner*—Alvin E. Tanenholtz
*Attorney, Agent, or Firm*—Lyon & Lyon

[57] ABSTRACT

The present invention provides antisera and monoclonal antibodies directed against the sporozoite stage of the malaria parasite capable of providing protection against infection in both animals and humans. The invention further provides a purified antigen derived from sporozoites of the malaria parasite, the antigen being suitable for use as a vaccine against malarial infections in both animals and humans. The invention further provides means for preparing said antigen and a vaccine comprising said antigen.

5 Claims, No Drawings

MALARIA VACCINE

BACKGROUND AND PRIOR ART

Malaria is a severely debilitating, widespread disease caused by infection by a parasite of the genus Plasmodium. Despite years of research and major expenditures for eradication or control, the disease remains a major world-wide public health problem, both for those living in areas where the disease is endemic and for travelers and visitors to such areas. Although once commonly encountered in the continental United States, the disease is now principally found in tropical and semitropical areas of the world including many developing nations.

The major species infective to humans are *Plasmodium falciparum* and *Plasmodium vivax*. Two other plasmodial species, *Plasmodium ovale* and *Plasmodium malarie*, occur with much less frequency, but the latter one may induce considerable immunopathology, particularly in children. Other species of the parasite are infective in other mammalian species.

The complex life cycle of the parasite is well understood in general outline, although much remains to be understood at the biochemical and genetic levels. In infected humans, the organism exists primarily as an intracellular parasite of red blood cells in which it undergoes vegetative reproduction. There is also a transient extracellular phase during which organisms migrate through the bloodstream to infect new host cells. (The synchronous rupture of large numbers of infected red blood cells, releasing free parasites, is frequently associated with fever). The blood forms of the parasite, both intra- and extra-cellular, are well adapted to the host, and elicit only an inadequate protective antibody response.

Malaria is transmitted by the bite of a mosquito. The mosquito functions as more than a passive vector for the parasite. The Plasmodium undergoes several stages of differentiation in the mosquito host, and also undergoes sexual mating. In the mosquito, the organism is first found in the gut, later in the hemocele of the thoracic region, and finally in the salivary glands from which they are injected into the human or other mammalian host when the mosquito next feeds. The differentiated form found in the salivary gland is referred to as a sporozoite. As the mosquito feeds, sporozoites enter the bloodstream where they exist transiently before entering primary target cells, presumably cells of the liver.

Attempts to control malaria have been partly but not wholly successful. The disease has been largely eliminated from areas where mosquito abatement and eradication programs have succeeded in removing or controlling the population of mosquito vectors. Nevertheless, the disease is still endemic in large portions of the world. No effective means of prevention for individuals who risk exposure to the disease has been found to date except by drug administration.

The major prior art strategy for the control or prevention of malarial infections in individuals has been based upon attempts to provide immunity against the blood forms of the parasite. The approach was considered advantageous because substantial amounts of experimental material could be obtained from in vitro cultures. Furthermore, if antibodies against the blood forms of Plasmodium could be obtained, they could be administered to patently infected individuals to suppress an ongoing infection. However, attempts to isolate and characterize a unique protective antigen from these forms have not been successful. Furthermore, clinical and experimental observations suggest that the blood forms may not be highly immunogenic.

A second prior art strategy, upon which the present invention is based, has been to attempt to develop antibodies capable of inactivating sporozoites, the primary infective agent. The chief disadvantage of this approach is that sporozoites may be obtained only from infected mosquitos, hence are available in extremely limited quantities. Moreover, it was originally assumed that antibodies to sporozoites would not be effective in preventing the establishment of infection. However, continued experimentation has been encouraged by the discovery that sporozoites, in contrast to the blood forms of Plasmodium, are highly antigenic.

The first demonstration that sporozoites were immunogenic and could be used to protect against infection was provided by Mulligan et al, *J.Malar.Inst.India*, 4, 25 (1941). Injections of killed *P. gallinaceum* sporozoites were shown to produce active immunization of fowls against avian malaria caused by the same organism. The results of this experiment were generally assumed to apply only in the case of avian malaria. No further studies on sporozoite immunogenicity were done until the pioneering work of co-inventor R. Nussenzweig was begun. In mice it was shown that sporozoites of *P. berghei*, inactivated by exposure to X-rays or gamma irradiation, could immunize these animals against the disease when challenged by inoculation of active sporozoites, Nussenzweig, R. S., et al., *Nature*, 216, 160 (1967); Vanderberg, J., et al., *J.Parasitol.*, 54, 1175 (1968); Nussenzweig, R., et al., *Mil.Med.*, 134, 1176 (1979). Immunity was found to be directed solely against sporozoites and the protected animals remained fully susceptible to infection when challenged with blood stages of the same parasite strain. It was also observed that the route of immunization was of primary importance, and that in the absence of adjuvants, a reproducibly high degree of protection could only be obtained upon repeated intravenous immunization, Spitalny, G., et al., *Proc.Helminthol.Soc.Wash.*, 39, 506 (1972), or through the repeated bite of infected irradiated mosquitoes, Vanderberg, J., et al., *J.Parasitol.*, 56, 350 (1970). It is important to note that only the later maturation stage in the mosquito vector (salivary gland sporozoites) was able to produce protective immunity. Antisera against earlier developmental stages, e.g., oocyst sporozoites, did not protect against mature sporozoites found in the mosquito's salivary glands, Vanderberg, J., et al. (1972), supra. The immunity provided by injection with irradiated sporozoites appears to be induced by both humoral and cell-mediated mechanisms. Circulating antibodies against irradiated sporozoites can inactivate non-irradiated sporozoites in vitro, such that they are unable to produce infection when subsequently injected into non-immune mice. Rats and mice readily produce antibodies to sporozoites of Plasmodial species infective to other animals, including *P. falciparum* and *P. vivax*, infective to man. However, these antisera do not cross-react with sporozoites of other malarial species and do not protect these animals against rodent infective strains. It has been noted, however, that different geographic isolates of the same species do cross-react extensively.

Sporozoite injection has been demonstrated to provide immunity in primates, i.e., rhesus monkeys inoculated with *P. cynomolgi* and *P. knowlesi*. Owing to the greater difficulty and expense of working with such experimental animals, the data relating to immunization of monkeys is necessarily less complete than for rodents. Early attempts to immunize rhesus monkeys against *P. cynomolgi* failed to demonstrate total protection against sporozoite challenge, Collins, W. E., et al., *Nat.New Biol.*, 236, 176 (1972); Ward, R. A., et al., *Proc.-Helminthol.Soc. Wash.*, 39, 525 (1972). The immunizing doses were of the order of a total of $1 \times 10^5$ sporozoites, a dose smaller than that previously determined necessary for successful immunization in the rodent system. Later results demonstrated that extensive or total protection could be achieved by administration of a total of $4 \times 10^7$ to $1.7 \times 10^8$ sporozoites over a period of 9.5 to 13.5 months, Chen, D., Ph.D. thesis, New York University School of Medicine, (1974). Protection against an otherwise lethal sporozoite-induced infection has also been obtained in a certain proportion of Rhesus monkeys immunized with irradiated sporozoites of *P. knowlesi* (Gwadz at al., *Bull. WHO Suppl.*, 1, 165–173).

In humans, five cases of successful immunization against *P. falciparum* through the bite of infected irradiated mosquitoes have been reported, Clyde, D. R., et al., *Am.J.Med.Sci.*, 266, 169 (1973); Rieckmann, K., et al., *Trans.R.Soc.Trp.Med.Hyg.*, 68, 258 (1974). The protection was fully effective against a number of geographic isolates of *P. falciparum*. No cross-reactivity with P. vivax was observed. However, one of the volunteers was subsequently also immunized against sporozoites of *P. vivax*. Protection in both cases lasted only for a period of a few months.

In addition to the principal facts regarding immunization with sporozoites, there has been developed in the prior art a substantial body of information of a fundamental nature, relating to the nature of the interaction between sporozoites and antibody, and the development of quantitative methods of measurement. Two methods of measurement are significant.

The circumsporozoite (CSP) reaction is observed under phase contrast light microscopy when mature infective sporozoites are incubated with antiserum. Viable sporozoites develop at their posterior end a threadlike precipitate which increases progressively in length, Vanderberg, J., et al., (1969), supra. The CSP reaction can be used to quantitate the antibody response of animals vaccinated with sporozoites, and can also be used to measure the relative infectivity of different sporozoite preparations. The existence of a CSP reaction in a vaccinated animal can in general be correlated with protective immunity; in the primate systems, lack of CSP activity indicates lack of protective immunity but in some instances in rodents, protection has been observed in the absence of CSP reaction.

The sporozoite neutralization reaction (SNA) is carried out by preincubating active sporozites with an antibody preparation, then challenging test animals with the anitbody-treated sporozoites. In primates the SNA reaction correlates well, both positively and negatively, with immunity. However, the tests are time-consuming and expensive to perform since test animals must be challenged, then monitored for the occurrence of patent malarial infection. The criteria for protection may be either complete resistance to an intravenous challenge with viable sporozoites or partial resistance resulting in delayed patency or an altered course of infection.

Standard techniques for measuring antigen antibody reactions are also applicable for the detection and quantitation of anti-sporozoite antibodies, including, for example, radioimmunoassay, immune precipitation, direct and indirect immunofluorescence reactions, and the like.

In addition to the foregoing prior art relating to the establishment of immunity to malarial infections and the nature of the immune reactions, the present invention employs a variety of techniques known in the art, including the preparation of monoclonal antibodies, and recombinant DNA methods. Such methods are described in detail or by reference in the detailed description and examples sections.

SUMMARY OF THE INVENTION

The present invention provides antisera and monoclonal antibodies directed against the sporozoite stage of the malaria parasite capable of providing protection against infection in both animals and humans. The invention further provides a purified antigen derived from sporozoites of the malaria parasite, the antigen being suitable for use as a vaccine against malarial infections in both animals and humans. The invention further provides means for preparing said antigen and a vaccine comprising said antigen.

DETAILED DESCRIPTION OF THE INVENTION

The present invention employs prior art methods for growing and maintaining mosquitoes (*Anopheles stephensi*), for propagating the parasite (Vanderberg, J. P., et al., *J.Parasitol.*, 54, 1009 (1968)), and for the preparation of X-irradiated mosquitoes for immunization, Vanderberg, J. P., et al., *J.Parasitol.*, 56 (Suppl), 350 (1970).

Sporozoites were purified from mosquito salivary glands by successive passage through columns containing Sepharose-6MB (trademark, Pharmacia, Inc., Piscataway, N.J.), that had been covalently coupled (a) to a thyroglobulin, and (b) to hog gastric mucin, and then incubated with excess concanavalin-A and wheat germ agglutinin. Most of the bacteria and mosquito debris adhered tightly to both columns. Sporozoites were recovered in 70 to 80 percent yield from the eluate. Antiserum was prepared from immunized mice by conventional techniques.

The present invention provides a variety of hybridoma cell lines, each producing monoclonal antibodies which are highly specific and capable of inactivating sporozoites of different species of malaria parasites. Hybridoma cells are produced by the artificial fusion of plasmacytoma cells of mouse origin with spleen cells of immunized mice or rats. The techniques for producing hybridoma cells was first described by Kohler, G., et al., *Nature*, 256, 495 (1975). Clones of hybridoma cells (arising from a single parent plasmacytoma-spleen fusion cell) are tested for their ability to produce the desired antibody. The selected clones are maintained in continuous culture. Each clone produces only a single antibody type and antibodies thereby produced are termed monoclonal. Monoclonal antibody preparations are therefore highly specific, being directed against a single antigen only. Furthermore, in contrast to conventional antibody preparations which typically include different types of antibodies directed against different sets of determinants on the same antigen, monoclonal antibody preparations are directed only against a single determinant. Monoclonal antibodies may be prepared from supernatants of cultured hybridoma cells or from ascites induced by intraperitoneal inoculation of hybrid cells into mice. The latter method is preferred since large amounts of antibody may be prepared thereby.

A principal aspect of the present invention is the isolation, purification and production of a sporozoite protein considered to be the major antigen for conferring protective immunity against malaria. This protein is part of a family of polypeptides of similar basic structure, but having sufficient variation depending upon the species of malaria parasite from which they have been isolated to be antigenically non-crossreactive. However, it was discovered as part of the present invention that the immunogenic protein of sporozoites from different Plasmodium species share common characteristics. They are proteins, which cover uniformly the plasma membrane of the parasite, with a molecular weight between 40,000 and 60,000 and a low isoelectric point, close to pH 4.0. These proteins constitute a homologous set of proteins and the principles of isolation and purification for a single member of the set, as described specifically in the Examples section, should apply generally to all members of the set with only minor variations or modifications of procedure obvious to those of ordinary skill in the art. The generic term applied to this class of sporozoite proteins is P-44, signifying their isolation from species of the genus Plasmodium and their approximate molecular weight of 44,000. Individual members of the group are further designated by their species initial, e.g., Pb-44, derived from *Plasmodium berghei;* Pk-44, derived from *Plasmodium knowlesi;* Pf-44, derived from *Plasmodium falciparum;* Pv-44, derived from Plasmodium vivax; and so forth. The P-44 proteins have been determined to be a major constituent of the outer coat of sporozoites isolated in late stages of maturation from the mosquito host. They consist of a single polypeptide chain, with a molecular weight between 40,000 and 50,000 as determined by electrophoresis in sodium dodecylsulfate polyacrylamide gel electrophoresis (SDS-PAGE) performed under reducing conditions. The proteins have a rather low isoelectric point, in the neighborhood of pH 4. The proteins do not appear to be glycosylated, and their isoelectric point is not affected by treatment with neuraminidase. The proteins can be used to elicit protective antibodies against the species from which they were derived.

The P-44 proteins may be purified from sporozoites prepared as described, supra. The sporozoites may be disrupted by a variety of means, using a French pressure cell or detergents (NP-40). The addition of protease inhibitors is necessary to prevent cleavage of P-44. The proteins are found in the supernatant obtained by centrifugation at 100,000 g. Further purification can be accomplished by any of a variety of techniques known in the art, taking advantage of the known properties of the proteins. A preferred method of purification involves the use of isoelectric focussing followed by affinity chromatography on a solid support (such as Sepharose beads) to which have been coupled hybridoma antibodies prepared against P-44 of the relevant species. P-44 proteins prepared by this method are essentially homogeneous as judged by SDS acrylamide gel electrophoresis.

Although the P-44 proteins may be prepared in a highly purified state by the foregoing procedure, the amounts which can be prepared are severely limited by the practical difficulties of obtaining large amounts of the sporozoite starting material. An alternative method for preparing the P-44 proteins is provided by the use of recombinant DNA techniques. In this method, a deoxynucleotide sequence coding for a P-44 protein is cloned in a microorganism such as *E. coli,* which may then be induced to express the protein during their normal growth and metabolism. In this circumstance, the only practical limitations on the amount of P-44 which may be obtained are dictated by the size of the fermentation equipment in which the bacteria or other microorganism are grown.

The deoxynucleotide sequence coding for P-44 may be obtained either directly from the sporozoite genome, or indirectly, by the cDNA technique. In the cDNA technique, messenger RNA (mRNA) is isolated from the sporozoites and DNA complementary thereto (cDNA) is synthesized using the enzyme reverse transcriptase, acting in the presence of the four deoxynucleoside triphosphates. The cDNA method is preferred because it is not presently known whether there are introns in the gene for P-44. The cDNA method is also advantageous because isolated mRNA may be fractionated and identified as coding for P-44, both on the basis of size and on the basis of activity in in vitro translation.

In the initial cloning, a major technical problem is to identify cDNA coding for P-44 out of a probable mixture of cDNAs, in the absence of data on the amino acid sequence of P-44. There are two basic approaches, which may be used separately or in conjunction to solve the problem. The first is prepurification of the isolated mRNA, to maximize the proportion of cDNA clones coding for P-44. The second is to insert the cDNA directly into an expression vector giving a reasonable probability of detectable expression, then selecting for colonies of transformed bacteria which yield P-44 as detected by an assay using the specific monoclonal antibodies.

Prepurification of mRNA may be carried out by sedimentation or gel electrophoresis, selecting mRNA of approximately 1500 bases in length.

If enough amino acid sequence data is known, preferably a sequence of at least 5–7 amino acids of P-44, it is feasible to synthesize an oligonucleotide coding for the known sequence. Any such oligonucleotide will have a substantial degree of base-pairing homology with the corresponding region of cDNA coding for P-44. Preferably, the chosen amino acid sequence is one in which amino acids coded by only one or two possible codons, e.g., methionine, tryptophan, histidine, asparagine, are a substantial part of the sequence. Such sequences are necessarily coded by a fairly unique oligonucleotide sequence, and the resulting homology between the synthetic sequence and the corresponding region of cDNA is maximized. The synthetic oligonucleotide appropriately radioactively labeled, is employed as a hybridization probe to identify cDNA coding for P-44. Preparative gel electrophoresis may then be employed to fractionate cDNA enriched for P-44 coding sequences.

Selection for expression may be carried out in a number of known expression vectors. For example, the plasmid pBR322 contains a single Pst I site located within the beta lactamase gene. If the cDNA is inserted at the Pst I site, using the GC "tailing" method, recombinant clones can be detected by loss of resistance to ampicillin and expression of a coding sequence inserted therein should occur with a probability of 1 in 6. If a protein is expressed, it may be made as a fusion protein coupled to the N-terminal segment of the beta lactamase gene. The latter comprises a signal peptide which can cause the expressed fusion protein to be transported to the periplasmic space from which it may be released by osmotic shock. See Villa-Komaroff, et al., *Proc.Nat.Acad.Sci.USA*, 75, 3727 (1978). Expression may be detected by analysis of hybridoma antibody reactive material in single colony isolates of transformed cells. Under certain circumstances, re-initiation of translation may occur at the GC-tailed insertion, leading to direct expression of proteins having an N-terminal methionine, Chang, A. C. Y., et al, *Proc.Nat.Acad.Sci.USA*, 77, 1442 (1980).

Because of the general structural similarity of the P-44 proteins, the foregoing identification procedure need only be carried out with the first species of cDNA isolated. Once cloned, the initial cDNA isolate can be employed as a hybridization probe due to substantial sequence homology between cDNAs coding for P-44 proteins from different Plasmodium species. The P-44 proteins may also be expressed directly, rather than as fusion proteins, by insertion into an expression vector constructed for direct expression of inserted coding sequences.

The P-44 proteins may be purified from bacterial extracts by the methods previously described for their purification from sporozoite extracts. Whether expressed directly or as fusion proteins, the P-44 proteins are reactive with the antisera and monoclonal antibody preparations previously described, and these may be employed for qualitative analysis and quantitative detection of the proteins. The major advantage of P-44 proteins prepared by recombinant DNA technique is that substantial amounts may thereby be made available for immunization of animals and man against malaria. Vaccines may be prepared comprising purified P-44 proteins in physiologically acceptable media at concentrations sufficient to provide active and long-lasting immunity. The course of immunization may be monitored by measuring antibody titre by the CSP reaction and indirect immunofluorescene during the course of immunization. The availability of sufficient P-44 protein makes it feasible to provide immunity as a result of a single injection, possibly followed by one or more booster shots.

Further details illustrating the practice of the invention are set forth in the following examples. Where the examples refer specifically to materials derived from a given plasmodium species, it will be understood by those skilled in the art that the techniques are applicable, essentially as described, for other Plasmodium species as well.

EXAMPLE 1

Isolation and characterization of monoclonal antibodies to Pb-44.

In general, the method described by Kohler, et al, supra, and a Pontecorvo, G., *Somatic Cell Genet.*, 1, 397 (1975) was employed with minor modifications. The procedure was carried out at room temperature. Spleen cells from BALB/c mice (obtained from Jackson Laboratories, Bar Harbor, Maine) immunized with *P. berghei*, as described supra, were obtained four days after the last booster. $1.4 \times 10^8$ washed spleen cells were mixed with $1.4 \times 10^7$ plasmacytoma cells (strain P3U1, provided by Dr. J. Unkeless, The Rockefeller University, New York) for fusion. After mixing, the cells were washed once by centrifugation in a conical glass tube with about 20 ml of Dulbecco's modified Eagle's medium (Grand Island Biological Company, Grand Island, N.Y.) that contained 20 mM Hepes buffer (Sigma Chemical Company, St. Louis, Mo.), pH 7.2, in serum-free medium at $200 \times g$ for 10 minutes. The pellet was resuspended gently in 1 ml of a solution that contained 35% (w/v) polyethylene glycol 1,000 (J. T. Baker Chemical Company, Philipsburg, Pa.) in RPMI-1640 medium (Microbiological Associates, Walkersville, Md.). Immediately afterwards, the cells were further diluted by adding, in succession, 3 mls of dulbecco's modified Eagle's medium over about 3 minutes, followed by 12 ml of the same medium containing 20% (v/v) horse serum over about 5 minutes. The tube was rotated slowly during this procedure. Subsequently, the cell suspension was centrifuged at $200 \times g$ for 10 minutes and resuspended in 50 ml of Dulbecco's modified Eagle's medium containing 10% (v/v) fetal calf serum, 1% (v/v) antibiotic-antimycotic solution (Grand Island Biological Company), $3 \times 10^{-4}$M thymidine and $10^{-3}$M hypoxanthine (both obtained from Sigma Chemical Company). The suspension was distributed in aliquots of about 50 µl per well in 96-well plates (Linbro Chemical Company, Hamden, Conn.) and 24 hours later 50 µl of Dulbecco's modified Eagle's medium containing fetal calf serum, antibiotic-antimycotic solution, thymidine and hypoxanthine as described, plus $10^{-5}$M aminopterin (Sigma Chemical Company) were added to each well. Supernatants were tested for the presence of antibodies to sporozoites by indirect immunofluorescence.

Supernatant samples were incubated in multiple-well slides containing gluteraldehyde-fixed sporozoites. The slides were then rinsed in phosphate-buffered saline (Grand Island Biological Company), stained with fluorescein-conjugated rabbit anti-mouse IgG (Meloy Laboratories Inc., Springfield, Va.), and counterstained with Evans' blue. Samples were examined at $25 \times$ magnification with an epi-illuminated microscope equipped with standard filters for fluorescence.

There was significant growth of cell colonies in 575 out of 859 wells seeded after fusion of the plasmacytoma cell line with spleen cells from mice immunized with *P. berghei* sporozoites. Five wells yielded supernatants that contained antibodies to sporozoites as detected by indirect immunofluorescence.

Monoclonal antibodies were purified in substantial quantity from ascites induced by intraperitoneal inoculation of hybridoma cells into BALB/c mice previously injected with pristane. The resulting ascitic fluid contained approximately 2 mg/ml antibodies to Pb 44. 100 ml of fluid was dialyzed against 0.01M Tris-HCl buffer, pH 8.6 that contained 0.02M NaCl, having a conductivity of 1.6 mS at 0° C. After centrifugation at $10,000 \times g$ for 30 minutes, the supernatant was loaded onto a 2.5 cm $\times$ 30 cm column of DEAE-Sephadex A-50 (trademark Pharmacia, Inc., Uppsala, Sweden) equilibrated in the same buffer. The column was washed extensively with the starting buffer until the OD at 280 nM of the eluate was less than 0.050. The column was then eluted with a linear gradient of NaCl, to 12 mS. The monoclonal antibodies eluted in a sharp peak in tubes with conductivities close to 5 mS. These fractions were pooled, concentrated and subjected to molecular-sieve chromatography on Sephadex G-200. The antibody activity was associated with the material eluted in the first OD peak. About 100 mg of antibodies were recovered.

Antibody can also be obtained from serum collected from mice 9-10 days after they were inoculated, either subcutaneously or intraperitoneally with $7 \times 10^8$ 3D11 hybridoma cells. Antibody obtained from any of the above sources was characterized by positive immunofluorescence and CSP reactions. Further, the antibody injected intraveneously afforded protection against infection by viable sporozoites. For example, 10 μg of antibody could protect a mouse against a challenge of $10^3$ sporozoites administered 30 minutes later. In animals receiving $10^4$ sporozoites, a dose of 300 μg was required to be fully protective. Where protection was less than complete and parasitemia was eventually observed, the prepatent period was prolonged in relation to controls.

EXAMPLE 2

Purification of Pb-44.

Sporozoites of *P. berghei* were first purified from infected mosquitoes as described, supra, using Sepharose-6MB columns having covalently coupled thyroglobulin and hog gastric mucin, followed by incubation with excess concanavalin A and wheat germ agglutinin. Sporozoites were recovered from the supernatants in 70–80% yield. In some experiments, partially purified sporozoites obtained at this stage were labelled with $^{125}$I by the lactoperoxidase method, then dialyzed overnight to remove free iodine. Protease inhibitors diisopropylfluorophosphate (4mM), aprotinin (2-trypsin-inhibiting units/ml), antipain and leupeptin (25 mg/ml) were added to the parasites before dialysis.

Partially purified sporozoites were disrupted with 0.2% NP-40 (Trademark, Particle Data Labs, Ltd., Elmhurst, Ill.) in the presence of the protease inhibitors and centrifuged at $10,000 \times g$. Diisopropylfluorophosphate (4 mM) was added to the supernatant, which was further purified by preparative isoelectric focussing, in a granulated dextran gel (Ultrodex, trademark, LKB-Produkter AB, Bromma, Sweden) using the L.K.B. multiphor kit and a mixture of ampholines of pH 3.5–5 and 5–7.

The Pb-44 protein (pI about 4) was further purified by affinity chromatography on CnBr-activated Sepharose (trademark Pharmacia, Inc., Uppsala, Sweden) beads to which monoclonal antibody to P-44, prepared as descrwas assayed by SDS-PAGE, followed by radioautography. The resulting Pb-44 preparation was essentially homogeneous, as judged by SDS-polyacrylamide gel electrophoresis.

The assay for the presence of Pb-44 was performed as follows. The fractions obtained during the purification were immunoprecipitated with monoclonal antibody following the procedure described by Kessler, S. W., *J.Immunol.*, 115, 1617 (1975), using a suspension of formaldehyde-treated *Staphylococcus aureus* to bind the immune complexes. For the binding reaction, Tris buffer at pH 8.6 containing 10% (w/v) *S. aureus* suspension was employed. Pb44 was eluted from the immune complexes with a mixture containing 2% (w/v) SDS, 10% (v/v) glycerol, 10% (v/v) 2-mercaptoethanol and 6M urea. The labelled eluate was then fractionated by electrophoresis on 10% (w/v) SDS-polyacrylamide gels which were radioautographed after fixation and drying by exposing the dried gels to X-omat R film (XR5) (trademark Eastman Kodak Company, Rochester, N.Y. ), and an image-intensifying screen (Cronex, trademark du Pont instruments, Wilmington, Del.) at −70° C.

The total radiolabelled extract of *P. berghei* was immunoprecipitated with a non-specific mouse myeloma protein (MOPC-21). Immunoprecipitation was performed with the monoclonal antibody to Pb-44. The purified preparation of Pb-44 was obtained after electrofocusing and affinity chromatography.

EXAMPLE 3

Cloning cDNA coding for a P-44 protein.

The techniques of recombinant DNA technology make extensive use of enzyme-catalyzed reactions. Purified enzymes for use in the practice of the present invention are currently available from commercial sources. Restriction endonucleases, their nomenclature and site specificity, have been described in detail by Roberts, R. J., *Nucl.Acids Res.*, 8, r63 (1980). The restriction enzymes used in this work are obtained from New England BioLabs, Beverly, Mass., and used in amounts and under reaction conditions specified by the manufacturer for each enzyme. Reverse transcriptase is provided by Dr. J. Beard, Life Sciences Inc., St. Petersburg, Fla. DNA polymerase I and T4 polynucleotide kinase are obtained from New England BioLabs, Beverly, Mass. Micrococcal S1 nuclease is obtained from Miles Laboratories, Elkhart, Ind. Bacterial alkaline phosphatase is obtained from Worthington Biochemical Corporation, Freehold, N.J. DNA polymerase I (Klenow modification) is obtained from Boehringer Mannheim GMBH, Indianapolis, Ind.

A total of 1000 infected mosquitoes, as described in Example 1, were collected, frozen quickly in liquid nitrogen and stored at −70° C. RNA was prepared essentially as described by Seeburg, P. H., et al.; *Cell*, 12, 157 (1977), and by Chirgwin, J. M., et al.; *Biochemistry*, 24, 5294 (1979). 0.1 grams of frozen tissue were added to 100 ml of 5M guanidine thiocyanate in 50 mM Tris-Cl, pH 7.5, 10 mM EDTA and 5% (w/V) 2-mercaptoethanol and homogenized until all the tissue was dispersed. The solution was centrifuged at 10,000 rpm for 10 minutes and the supernatant adjusted to 2% (w/v) Sarkosyl (trademark, ICN Pharmaceuticals, Planeview, N.Y.), and heated at 65° C. for two minutes. Cesium chloride was then added (0.1 g/ml of solution) and the resulting solution was layered over 6 ml cushions of half-saturated CsCl in 10 mM EDTA in SW27 cellulose nitrate tubes. Centrifugation was at 25,000 rpm for 16 h at 20° C. The RNA pellet was dissolved in 5 mM EDTA, 0.5% (w/v) Sarkosyl and 5% (w/v) 2-mercaptoethanol, extracted with phenol and chloroform and precipitated with ethanol. Usually, 0.5–1 mg of RNA were obtained per g of tissue. The RNA was then passed over an oligo(dT)-cellulose column (Aviv, H., et al., *Proc.Nat.Acad.Sci.USA*, 69, 1408 (1972)), to enrich for the polyadenylated fraction.

A sample of mRNA isolated as described was translated in vitro using a translation system isolated from wheat germ (Roberts, B. E., et al., *Proc.Nat.Acad.Sci.USA*, 70, 2330 (1973)). Proteins produced by in vitro translation were immunoprecipitated as described in Example 2, and fractionated on an SDS-polyacrylamide gel as described in Example 2. mRNA fractions containing sequences coding for P-44 can be identified by this means.

Prior to cDNA synthesis, the mRNA is fractionated by preparative gel electrophoresis to enrich for mRNA on the order of 1500–2000 nucleotides in length.

For preparative synthesis of cDNA, polyadenylated, fractionated mRNA is incubated in 200 μl reactions containing 50 mM Tris-Cl, pH 8.3 10 mM $MgCl_2$, 20 mM KCl, 10 mM 2-mercaptoethanol, 500 μM each of dATP, dCTP, dGTP and dTTP (one [$\alpha$-$^{32}$P]-nucleoside triphosphate at specific activity 500 cpm $^{32}$P per pmol), 20 $\mu$g/$\mu$l oligo(dT)$_{12-18}$ and 200 units reverse transcriptase. Incubation is at 42° C. for 30 minutes and is stopped by the addition of EDTA to 10 mM. After extraction with phenol and chloroform and precipitation by ethanol, the material is fractionated on a 25×0.25 cm column of Sephadex (trademark Pharmacia, Inc., Uppsala, Sweden) G-50 in 1 mM Tris-Cl, pH 7.4, and 0.01 mM EDTA. The leading peak is collected (~200 $\mu$l) and adjusted to 0.3M NaOH and 10 mM EDTA and incubated overnight at room temperature. Following neutralization with sodium acetate, pH 5.5, and ethanol precipitation, the second strand is synthesized in a 50-$\mu$l reaction containing the same buffer as described above, 500 $\mu$M each of dATP, dGTP, dTTP and 100 $\mu$M dCTP (10,000 cpm $^{32}$P per pmol) and 50 units reverse transcriptase. Incubation is at 42° C. for 90 minutes. For subsequent restriction enzyme analysis the reaction is stopped by heating to 65° C. for 10 minutes and the appropriate restriction enzymes added directly. Alternatively, the reaction products may be fractionated as described above on a Sephadex G-50 column and the peak evaporated to dryness before proceeding to treatment with S$_1$ nuclease.

After fractionation by Sephadex G-50, the double stranded cDNA is incubated with 5 units of S$_1$ nuclease in 300 mM NaCl, 30 mM Na acetate, pH 4.5, and 3 mM ZnCl$_2$ for 41° C. for 5 minutes. The reaction is stopped by the addition of EDTA to 10 mM and neutralized with Tris base.

Trimmed ds-CDNA is then tailed using calf thymus terminal transferase in a 30 minute reaction at 37° C. containing 140 mM K cacodylate, 30 mM Tris base (pH 7.8), 1 mM CoCl$_2$, 0.1 mM DTT, 25 $\mu$M dCTP ($\alpha^{32}$P-dCTP, 8.36 $\mu$Ci/nmole), and 150 units terminal transferase/$\mu$g ds-cDNA. The tailing reaction is described, generally, by Roychoudhury, R., et al., *Nucl.Acids Res.*, 3, 101 (1976). Approximately 30 bases are added to the 3' end under these conditions. Plasmid pBR322 is cleaved by Pst I endonuclease and provided with dG tails by the previously described tailing reaction, except that dGTP is used instead of dCTP, and no radioactive label is employed. Equimolar amounts of dC tailed cDNA and dG tailed pBR322 are annealed at a concentration of 1 $\mu$g/ml, using sequential 2 hour incubations at 42° C., 30° C., and 14° C. The hybrid plasmid DNA was ethanol-precipitated and then used to transform *E. coli* $\chi$1776 and selected for tetracycline resistance.

Colonies transformed by insert-bearing pBR322, as indicated by resistance to tetracycline and sensitivity to ampicillin are then screened for expression of P-44. Expression is detected by radioimmunoscreening, essentially as described by Meagher, R. B., et al; *Cell*, 10, 521 (1977), and by Broome, S., et al; *Proc.Nat.Acad.-Sci.USA*, 75, 2746 (1978). In this technique, individual colonies expressing a given protein may be detected in situ by means of a plastic film overlay to which monoclonal antibody to Pb-44 has been affixed. The tailing reaction produces ends of varied length, so that the probability of cDNA insertion in reading frame phase with the $\beta$-lactamase gene at the insertion site of pBR322 is 1 in 3. In addition, there is a probability of correct orientation of the insert of 1 in 2. Therefore, successful expression of a given cloned coding sequence can occur with a probability of 1 in 6, and the observed expression frequency will be 1/6th multiplied by the proportion of P-44 coding sequences in the cDNA preparation. On the basis of these considerations, at least 100 colonies, and preferably more, are screened for expression of P-44 by radioimmune screening.

Direct expression of the cloned coding sequence may occur at the dG-tailed Pst I site, as described by Chang, A. C. Y., et al, supra. Therefore, a somewhat higher frequency of expression than 1/6 may be observed.

The radioimmune screening procedure yields a certain proportion of false positive results. Therefore, colonies on replica plates corresponding to positive colonies in the radioimmune screening test are retested by the immunofluorescence technique described, supra, using small cultures.

Colonies yielding confirmed expression of protein reactive with the monoclonal antibody of Example 1 are further tested to determine whether the expression product, a $\beta$-lactamase-P-44 fusion protein, includes the entire P-44 sequence or merely a portion. For this purpose, SDS acrylamide gel electrophoresis of labelled, immunoprecipitable protein, essentially as described in Example 2, is performed. The $\beta$-lactamase fragment comprising the N-terminal portion of the fusion protein has an approproximate molecular weight of 18,000. A full-sized fusion protein should therefore have a molecular weight of approximately 62,000. Clones expressing an immunoreactive fusion protein in the molecular weight range of 60,000–70,000 are selected for nucleotide sequence analysis of the cloned insert, from which the amino acid sequence of P-44 may be predicted.

Once a clone expressing an immunochemically reactive P-44 fusion protein, preferably comprising the entire P-44 sequence, has been identified, the inserted cDNA sequence can be employed as a hybridization probe to identify cDNA coding for P-44 proteins isolated from other Plasmodium species. The cDNA can also be employed to purify mRNA coding for the P-44 proteins of other species by hybridization. Therefore, once the first cDNA sequence coding for P-44 or a fragment thereof is cloned, the subsequent isolation and purification of other species cDNAs is substantially simplified.

EXAMPLE 4

An oligonucleotide probe substantially complementary to a segment of cDNA coding for P-44 is chemically synthesized by the triester method, as described by Itakura, K., et al.; *J.Am.Chem.Soc.*, 97, 7327 (1975) and Itakura, K., et al.; *J.Biol.Chem.*, 250, 4592 (1975). The nucleotide sequence to be synthesized is determined from partial amino acid sequence data on P-44.

Partial amino acid sequences of P-44 are obtained by a micro-sequence method previously described by Shaw, et al.; *Nature*, 272, 510 (1978) and in *Solid Phase Methods in Protein Sequence Analysis* (Previero and M. Coletti-Previero, eds.), North Holland Amsterdam, article by Walter, J. E., et al., pp. 277–285 and by Capra, J. D., et al., pp. 69–80. Radiolabelled P-44 is purified as described in Example 2 from sporozoites fed with $^{14}$C-amino acid mixtures. The N-terminal P-44 sequence, or an internal sequence of tryptic peptides may also be obtained by standard amino acid sequencing methods (see, e.g., Stark, G. R., *Advan.Protein Chem.*, 24, 261 (1970) and articles in *Mol.Biol.Biochem.Biophys.*, 25 (1977). The tryptic peptides arising from P-44 are identified using radiolabelled P-44 as a carrier. It is preferred to synthesize an oligonucleotide complementary to a region of mRNA or cDNA coding for an amino acid sequence for which the number of codon choices is minimal. For example, amino acid sequences containing one or more tryptophan, methionine, histidine or asparagine residues will provide fairly unique oligonucleotide coding sequences. Such oligonucleotides are highly homologous to their cDNA counterpart. Once a fairly unique coding sequence is determined, the complementary sequence thereto is synthesized by the above-described process.

The synthetic oligonucleotide sequence is radiolabelled by any suitable method known in the art, e.g., by incorporating $^{32}P$ at the 5' end using $\gamma$-$^{32}P$ labelled ATP in a polynucleotide kinase-catalyzed reaction.

The labelled synthetic oligonucleotide is used to prime the synthesis of probe-cDNA from sporozoite mRNA, in a reverse-transcriptase catalized reaction, essentially as described by Chan, S. J., et al; Proc.Nat.Acad.Sci.USA, 76, 5036 (1979). The reverse transcriptase reaction mixture contains 50 mM Tris-HCl, pH 8.3, 35 mM KCl, 10 mM $MgCl_2$, 1 mM dithiothreitol, sporozoite polyadenylated mRNA, prepared as described in Example 3, 200 µg/ml, synthetic oligonucleotide primer, 50 µg/ml, 200 µm each of the four unlabeled deoxynucleoside triphosphates (dATP, dGTP, dCTP and TTP) and 200 µCi/ml of a [$^3H$]-labeled deoxynucleoside triphosphate, e.g., [$^3H$] dCTP. The reaction is begun by addition of 400 units/ml reverse transcriptase (obtained from Dr. J. W. Beard, Life Sciences Inc., St. Petersburg, Fla.) and the reaction mixture is incubated at 42° C. for 30 minutes. The reaction product, a cDNA-RNA hybrid, is removed by phenol extraction and ethanol precipitation. The RNA is removed by hydrolysis in 0.1M NaOH for 15 minutes at 70° C. After neutralization, single-stranded cDNA is separated from the reaction mixture by ethanol precipitation. The cDNA is then labeled with [$\gamma$-$^{32}P$]ATP using polynucleotide kinase as described, supra. Modifications of the above-described reaction conditions may be made in accordance with principles known in the art. Variations of pH, ionic strength and buffer composition are permissible within the limits known for activity of reverse transcriptase and for stability of the mRNA-primer complex. Similarly, conditions such as temperature, enzyme concentration and reaction time may be varied according to the known effects of these parameters on reaction rate, initiation rate and the like. For example, the reverse transcriptase reaction conditions described in Example 3 may be substituted for those given, supra.

The resulting probe-cDNA is employed in one of two ways. In a preferred alternative, double-stranded cDNA derived from sporozoite polyadenylated mRNA as described in Example 3 is first cloned into a suitable transfer vector. Cloning into pBR322 at the Pst I site as described in Example 3 may be employed. Other suitable plasmid or bacteriophase vectors such as pSC101, pBR313, $\gamma$Charon 16A, $\gamma$gtWES.$\gamma\beta$ are suitable, using appropriate insertion sites therefor and employing suitable insertion linkers as described by Scheller, R. H., et al., Science, 196, 177 (1977), many of which are commercially available, e.g., from Collaborative Research, Waltham, Mass. For a current list of NIH-approved transfer vectors, see Recombinant DNA Technical Bulletin, 3, No. 1, August 1980 (NIH Publication 80-99; U.S. Dept. of Health and Human Services). Transfer vectors bearing inserted cDNA are used to transform a host cell strain, such as E. coli HB101 or E. coli RR1. Single colonies of transformed cells containing P-44 cDNA inserts are identified using the labeled probe-cDNA in the in situ hybridization procedure described by Grunstein, M. and Hogness, D. S., Proc.Nat.Acad.Sci.USA, 72, 3961 (1975).

In an alternative procedure, the probe-cDNA is employed prior to cloning to identify the P-44 cDNA present among the reverse transcriptase reaction products where the template is polyadenylated sporozoite mRNA. In this alternative procedure, cDNA is first fractionated by gel electrophoresis and the P-44 cDNA identified by hybridization with [$^{32}P$]-probe-cDNA, as described by Southern, E. M., J.Mol.Biol., 98, 503 (1975). Fractions identified as containing P-44 coding sequences are purified by preparative gel electrophoresis and inserted in a suitable transfer vector, as described, supra.

EXAMPLE 5

Direct expression of P-44 proteins, rather than expression as a fusion protein, is accomplished by the use of an appropriate expression vector, suited for direct expression, once the cloned cDNA has been modified to remove the majority of any 5' untranslated portion. This in turn depends upon knowledge of the nucleotide sequence of the cloned cDNA, which is obtained either by the method of Maxam, A., et al.; Proc.Nat.Acad.Sci.USA, 74, 560 (1977), or by the chain termination method (Maat, J., et al.; Nucleic Acids Res., 5, 4537 (1978).

The underlying principle of direct expression is that the inserted DNA segment entirely replaces the coding segment normally transcribed and translated by the bacterial control region. The essential component of the control region preserved includes a promoter and a ribosomal binding site capable of acting in the host organism, and is termed the expression unit. As a practical matter, it is not necessary to remove precisely the nucleotides coding for the host portion of the fusion protein. The relationship between the ribosomal binding site and the start codon (AUG) is such that the start codon may be located anywhere within about 3-11 nucleotides of the ribosomal binding site (Shine et al., Proc.Nat.Acad.Sci.USA, 71, 1342 (1974); Steitz, J., et al., Proc.Nat.Acad.Sci.USA, 72, 4734 (1975)). Within this approximately 3-11 nucleotide region, the first AUG to be encountered sets the reading frame for translation. If the cloned cDNA coding for P-44 starts with an AUG codon, direct expression can occur when the cloned segment is inserted such that the AUG is 3-11 nucleotides from the expression unit. See Chang, A. C. Y., et al.; supra, Goeddel, D. V., et al.; Nature, 281, 544 (1979), and Roberts. T. M., et al.; Proc.Nat.Acad.Sci.USA, 76, 5596 (1979). If an AUG codon is not present, it can be provided by attaching an appropriate oligonucleotide linker, chemically synthesized, by blunt-end ligation. The latter method is preferred. The P-44 proteins are found on the outer surface of the sporozoite. The primary translation product is therefore a protein comprising an N-terminal signal peptide which is ordinarily removed by posttranslational processing during transport to the outer cell surface. Consequently, to achieve direct expression of P-44 in a bacterial system, it is preferred to modify the cDNA by removing, in addition to the 5' untranslated region, that portion of the cDNA coding for the P-44 signal peptide. The 5' end of the P-44 coding sequence is then provided with a 5' terminal ATG sequence to provide a signal for the initiation of translation.

The necessary modifications of the P-44 coding sequence are accomplished either by controlled digestion of the 5' end of the insert using a 3' exonuclease or T4 DNA polymerase, or by the combination of restriction endonuclease cleavage at a point to the 3' side of the desired starting point followed by chemical synthesis to restore as much of the desired coding sequence as necessary. Controlled digestion is preferably carried out using T4 polymerase, which in the absence of added deoxynucleoside triphosphates, catalyzes 3'–5' exonucleolytic digestion of double-stranded DNA (Englund, P. T., *J.Biol.Chem.*, 346, 3269 (1971)). The extent of digestion is controlled by selection of proper temperature, reaction time and amount of enzyme, according to principles well known in the art. Experimentation will be necessary in each instance, since optimal reaction conditions must be determined for each lot of enzyme and for each DNA to be modified. Termination of digestion at a predetermined stopping point is achieved by including a single deoxynucleoside triphosphate in the reaction mixture, corresponding to the desired stopping point. For example, in the presence of dATP, DNA is digested from 3' to 5' until the polymerase reaches a dA residue, at which point further net digestion ceases. Several cycles of digestion, each with its predetermined stopping point, can be carried out in sequence, to construct DNA molecules having a predetermined end point. Exonucleolytic digestion with T4 polymerase affects only the strands having 3' termini. The complementary strands remain as unpaired, single-stranded tails, which must also be removed. $S_1$ nuclease is the preferred enzyme for the purpose. The product of combined treatment with T4 polymerase and $S_1$ nuclease is blunt-ended, double-stranded DNA.

Chemical synthesis of deoxynucleotide sequences used to replace segments cleaved by restriction endonuclease digestion is carried out, for example, as described by Itakura, K., et al.; *J.Biol.Chem.*, 250, 4592 (1975) and Itakura, K., et al.; *J.Am.Chem.Soc.*, 97, 7327 (1975).

Transfer vectors for direct expression are prepared by modifications of any of the known expression vectors for which the nucleotide sequence in the region adjacent to the promoter of the ribosome binding site is known, by means of the modification procedures just described. Preferably, both the modified insert and the modified expression vector are provided with a specific linker oligonucleotide containing a restriction site sequence, as described by Scheller, et al., *Science*, 196, 177 (1977).

Directly expressed P-44 proteins are purified from lysates of transformed cells essentially as described in Example 2.

As an alternative to direct expression of P-44 with no signal peptide, the protein is obtained from cultures expressing the pre-P-44 protein containing a signal peptide by means of an in vitro processing step. In vitro removal of the signal peptide is carried out by treating the protein extracted from transformed, induced cells, with a preparation of "rough" microsomes, as described by Jackson, R. C., et al.; *Proc.Nat.Acad.Sci.USA*, 74, 5598 (1977). The alternative procedure is advantageous in the situation where it is unclear where the signal peptide ends and the excreted product begins, as may be the case where the N-terminal amino acid sequence of a P-44 protein is unknown.

Expression of a P-44 fusion protein can be achieved without advance information on the nucleotide sequence of the cloned P-44 cDNA. Expression vectors are presently available having insertion sites in either the $\beta$-galactosidase gene or in the tryptophan operon D-protein in each of the three possible reading frames. See Hallewell, R., et al., *Gene*, 9, 27 (1980).

Insertion of the cloned P-44 cDNA in one of the three reading yields expression of a P-44 fusion protein, either coupled to an N-terminal portion of the trpD gene product or of $\beta$-galactosidase. Expression is detected by radioimmunoassay, as described in Example 3. Alternatively, the cDNA to be inserted is modified by the attachment of linker sequences of varied length, for example, of 8, 9 or 10 base pair lengths, thereby providing for insertion in correct reading frame in a single expression vector.

EXAMPLE 6

Vaccination with P-44 fusion protein. P-44 fusion protein is used without further modification to vaccinate animals, including humans, against the malaria species from which they are derived. The techniques of immunization, dose, route of administration, and vaccine compositions are determined according to principles well known in the art. A vaccine comprises P-44 or a P-44-fusion protein, a pharmaceutically acceptable diluent and, optionally, an adjuvant.

GENERAL CONCLUDING REMARKS

It will be understood by those skilled in the art that the present invention, the techniques and principles disclosed herein, are susceptible to modification by those of ordinary skill in the art and that the present invention is intended to include in scope all such modifications, extensions, etc., as come within the scope of ordinary skill. In particular, the choice of transfer vectors and expression vectors having advantageous properties such as high rates of expression, secretion of the expressed protein through the cell membrane, maximum stability, maximum antigenicity of the fusion protein, and the like, is deemed a matter of ordinary skill within the scope of the present invention. Specific examples directed to specific vectors, microorganisms and Plasmodium species are intended to illustrate the practice of the invention, and not to limit the scope thereof.

What is claimed is:

1. An antigenic protein consisting essentially of a sporozoite polypeptide selected from the group consisting of Pb-44, derived from *Plasmodium berghei;* Pk-44, derived from *Plasmodium knowlesi;* Pf-44, derived from *Plasmodium falciparum;* and Pv-44, derived from *Plasmodium vivax;* in purified form.

2. The antigenic protein of claim 1, consisting essentially of Pb-44 in purified form.

3. The antigenic protein of claim 1, consisting essentially of Pk-44 in purified form.

4. The antigenic protein of claim 1, consisting essentially of Pf-44 in purified form.

5. The antigenic protein of claim 1, consisting essentially of Pv-44 in purified form.

* * * * *

UNITED STATES PATENT AND TRADEMARK OFFICE
CERTIFICATE OF CORRECTION

PATENT NO. : 4,466,917

DATED : August 21, 1984

INVENTOR(S) : Ruth S. Nussenzweig and Victor Nussenzweig

It is certified that error appears in the above-identified patent and that said Letters Patent are hereby corrected as shown below:

In the heading [75] Inventors should read:

-- Ruth S. Nussenzweig
Victor Nussenzweig, both of New York, N.Y. --.

Signed and Sealed this

Eighth Day of January 1985

[SEAL]

Attest:

GERALD J. MOSSINGHOFF

Attesting Officer

Commissioner of Patents and Trademarks